United States Patent [19]

Inoue et al.

[11] Patent Number: 5,039,519

[45] Date of Patent: Aug. 13, 1991

[54] HAIR COSMETIC COMPOSITION

[75] Inventors: Takeshi Inoue, Utsunomiya; Tadasu Hikichi, Yachiyo; Yukihiro Fukuyama; Akihiro Kondo, both of Wakayama, all of Japan

[73] Assignee: Kao Corporation, Tokyo, Japan

[21] Appl. No.: 542,704

[22] Filed: Jun. 11, 1990

Related U.S. Application Data

[62] Division of Ser. No. 181,173, Apr. 13, 1988.

[30] Foreign Application Priority Data

Apr. 21, 1987 [JP] Japan .................................. 62-98234

[51] Int. Cl.$^5$ .......................... A61K 7/06; A61K 7/09; A61K 31/74
[52] U.S. Cl. ........................................ 424/70; 424/71; 424/78; 525/57; 525/59
[58] Field of Search ............... 424/70, 71, 78; 525/57, 525/59

[56] References Cited

U.S. PATENT DOCUMENTS

| | | | |
|---|---|---|---|
| 2,430,109 | 11/1947 | Dalelio | 526/324 |
| 2,431,373 | 11/1947 | Dalelio | 526/324 |
| 2,810,716 | 10/1957 | Markus | 526/329.1 |
| 3,551,357 | 12/1970 | Corte et al. | 526/324 |
| 3,957,741 | 5/1976 | Rembaum et al. | 526/324 |
| 4,229,549 | 10/1980 | Usauir et al. | 526/329.1 |
| 4,957,992 | 9/1990 | Inoue et al. | 526/324 |

FOREIGN PATENT DOCUMENTS

| | | | |
|---|---|---|---|
| 0022982 | 1/1981 | European Pat. Off. | 526/329.1 |
| 0122586 | 10/1984 | European Pat. Off. | 526/329.1 |
| 0243722 | 11/1987 | European Pat. Off. | 526/329.1 |
| 0214136 | 10/1984 | Fed. Rep. of Germany | 526/329.1 |
| 61-1095005 | 5/1986 | Japan | 526/329.1 |
| 61-176604 | 8/1986 | Japan | 526/329.1 |

*Primary Examiner*—Joseph L. Schofer
*Assistant Examiner*—N. Sarofim
*Attorney, Agent, or Firm*—Oblon, Spivak, McClelland, Maier & Neustadt

[57] ABSTRACT

A hair cosmetic composition comprising fine particles of a crosslinked polymer, which are insoluble in water and ethanol and do not form a film at normal temperature, is disclosed. A conventionally known film-forming polymer may also be formulated optionally. The hair cosmetic is free from stiffness, stickiness, or excessive gloss imparted to the hair which are the defects of conventional hair cosmetics using only conventional film-forming polymers, and provides excellent hair conditioning and hair-resetting effects.

2 Claims, No Drawings

HAIR COSMETIC COMPOSITION

This is a division of application Ser. No. 181,173, filed on Apr. 13, 1988.

BACKGROUND OF THE INVENTION

1. Field of the Invention

This invention relates to a hair cosmetic composition and, more particularly, to a hair cosmetic composition comprising fine particles of a specific type of crosslinked polymer which is insoluble in water and ethanol. The cosmetic composition produces an excellent hair conditioning effect, provides a satisfactory feeling to the hair set using the same, and makes it possible to easily reset the hair.

2. Description of the Background

Conventionally, film-forming polymers, such as polyvinyl pyrrolidone, polyvinyl pyrrolidone-vinyl acetate copolymer, vinyl acetate-crotonic acid copolymer, polyvinylmethyl ether-maleic acid half-ester copolymer, carboxylated vinyl acetate copolymer, acrylic resins (both of anionic and amphoteric types), or the like are used for hair cosmetic compositions for setting or conditioning the hair. These film-forming polymers are used as a solution dissolved in a solvent such as water, ethanol, or the like. A propellant is sometimes formulated into such solutions. Upon application or dispersion onto the hair, these polymers or resins produce a film, which can assist fixing the hair.

Characteristics demanded of such hair cosmetic compositions are a sufficient curl-retention capability and the provision of a satisfactory feeling hair-set. Providing a poorly finished feeling accompanied by stiffness is, however, a defect of conventionally available hair cosmetic compositions. Moreover, in highly humid conditions, these known cosmetics rapidly lose their hair conditioning capability.

Besides the film-forming polymers, water- or ethanol-soluble oils such as polyoxyalkylene derivatives or their phosphoric acid esters are known in the art as hair-conditioning components. Although hair cosmetic compositions using these oils as hair-conditioning components do not impart a stiff feeling, they do produce stickiness or excessive glossiness to the hair.

In order to overcome these defects prevalent in conventional hair-conditioning components, an attempt to use them in combination with a variety of other components has been undertaken. However, a hair cosmetic free from the defects of stiff, stick, or excessive gloss imparted to the hair and having an excellent hair conditioning effect has yet to be developed.

In view of these circumstances, the present inventors conducted extensive studies, and found that the above-mentioned problems could be overcome by using fine particles of specific crosslinked polymers insoluble in water and ethanol as a hair-conditioning component. The inventors further found that a better hair conditioning effect and a hair-resetting capability could be obtained by formulating such a crosslinked polymer in conjunction with a conventionally known film-forming polymer. Such findings have led to the completion of this invention.

SUMMARY OF THE INVENTION

Accordingly, an object of this invention is to provide, as a first invention, a hair cosmetic composition comprising fine particles of a crosslinked polymer which is derived from a monofunctional oil-soluble monomer having one ethylenically unsaturated bond, of which polymer having a glass transition point of not higher than 300° K., are insoluble in water and ethanol, and do not form a film at normal temperature.

Another object of this invention is to provide, as a second invention, a hair cosmetic composition containing, in addition to the aforementioned crosslinked polymer, a conventionally known film-forming polymer.

Other objects, features, and advantages of this invention will appear more fully from the following description.

DETAILED DESCRIPTION OF THE INVENTION AND PREFERRED EMBODIMENTS

Fine particles of water- and ethanol-insoluble, crosslinked polymers (hereinafter referred to simply as "fine polymer particles") to be used in this invention can be prepared by copolymerizing a monofunctional oil-soluble monomer and a polyfunctional oil-soluble monomer, which are mentioned below, by conventional suspension, dispersion, or emulsion polymerization.

Crosslinking may be effected either by copolymerizing a monofunctional oil-soluble monomer with a suitable polyfunctional oil-soluble monomer, or by bridging homopolymers which are produced using a suitable method. Alternatively, monomers to be polymerized or the polymerization conditions can be selected such that self-bridging takes place. Monomers having two or more ethylenically unsaturated bonds can advantageously be employed as a polyfunctional oil-soluble monomer.

Enumerated as examples of monomers which can be used in this invention as the monofunctional oil-soluble monomer having one ethylenically unsaturated bond, of which polymer having a glass transition point of not higher than 300° K., are acrylic esters such as ethyl acrylate, propyl acrylate, n-butyl acrylate, tert-butyl acrylate, sec-butyl acrylate, n-hexyl acrylate, cyclohexyl acrylate, n-octyl acrylate, 2-ethylhexyl acrylate, and n-lauryl acrylate; methacrylic esters such as n-butyl methacrylate, n-hexyl methacrylate, n-octyl methacrylate, 2-ethylhexyl methacrylate, and n-lauryl methacrylate; vinyl ethers such as methyl vinyl ether and ethyl vinyl ether; and vinyl esters.

Polyfunctional oil-soluble monomers having two or more ethylenically unsaturated bonds which can be employed in this invention include, for example, divinyl benzene, ethylene glycol diacrylate, ethylene glycol dimethacrylate, and trimethylol-propane acrylate, and the like.

It is desirable to use 0.03–10 parts by weight, preferably 0.2–2 parts by weight, of such a polyfunctional oil-soluble monomer per 100 parts by weight of the monofunctional oil-soluble monomer. When the proportion of the polyfunctional oil-soluble monomer exceeds 10 parts by weight, the resulting products exhibit only a poor hair conditioning effect. When the proportion is less than 0.03 part by weight, on the other hand, the copolymer obtained is soluble in water or ethanol, which produces a hair cosmetic composition with a poor feeling to the touch. Also, such a hair cosmetic composition does not have a hair re-setting ability.

Particle sizes of fine particulate crosslinked polymers produced from the above-mentioned monofunctional oil-soluble monomer and polyfunctional oil-soluble monomer are dependent upon the preparation methods employed, and can be adjusted to any preferred sizes in the range of 0.01 μm–5,000 μm. In view of the hair conditioning effect and the resulting feeling to the touch, it is desirable that the weight average particle size be 0.1–10 μm, and 1–5 μm in particular. For the purpose of preparing a crosslinked polymer with particle sizes in this desirable range, suspension polymerization may be employed as the polymerization method. Preparation of fine particles of a crosslinked polymer by suspension polymerization requires that the polymerization be effected under conditions that the monomers, in which a polymerization initiator is dissolved, are suspended in water in the presence of a dispersion stabilizer.

Any conventionally utilized oil soluble polymerization initiator may be used in copolymerizing the above oil-soluble monomers. Examples of such oil-soluble polymerization initiators include peroxy- or azobis-type initiators such as peroxybenzoyl, peroxylauroyl, 2,2'-azobisisobutylonitrile, 2,2'-azobis-(2,4-dimethyl-valeronitrile), o-chloroperoxybenzoyl, o-methoxyperoxybenzoyl, and the like.

In addition, the dispersion stabilizer used in the above reaction of oil-soluble monomers may be any conventionally utilized oil-soluble polymeric compounds, including, for example, water soluble polymeric compounds such as gelatin, starch, hydroxyethyl cellulose, carboxymethyl cellulose, polyvinyl pyrrolidone, polyvinyl alkylether, and polyvinyl alcohol; inorganic materials scarcely soluble in water such as barium sulfate, calcium sulfate, barium carbonate, calcium carbonate, magnesium carbonate, and calcium phosphate; surface active agents such as sodium laurylsulfate, sodium cetylsulfate, sodium polyoxyethylenelaurylether; and the like.

Dispersion of oil soluble monomers can be made according to a generally utilized method of dispersion, for example, by conventional stirring of various kinds of reinforced agitation using a mixer. The appropriate polymerization temperature varies depending on the polymerization initiator employed, although a temperature in the range of 25°–90° C. is usually applicable. Needless to say, the polymerization temperature employed must be lower than the boiling point of the monomers and other low-molecular weight compounds involved in the reaction.

The water phase is removed from fine polymer particles thus prepared by filtration. The filtrate is then washed with water and/or a low-boiling point solvent, with which high-boiling point, low-molecular weight compounds in the product are replaced. Subsequently, the polymer is dried by means of any conventional drying method such as spray-drying or vacuum drying, and collected as a powder.

Among fine particles of a crosslinked polymer used in this invention, those having an adhesion of 8–100 g.f/cm and modulus of elasticity of $5\times10^5 - 30\times10^5$ dyn/cm$^2$ are particularly desirable. If the polymer has an adhesion of less than 8 g.f/cm, it can exhibit only inadequate adhesion to the hair. The adhesion between polymer particles also decreases. These tends to result in release of the polymer particles from the hair when combing, and decreases the hair setting or re-setting capability. If the adhesion is more than 100 g.f/cm, on the other hand, fine particles of the polymer tends to be fused each other. This impairs the hair re-setting capability of the polymer, and gives an unacceptable sticky feeling to the users. If the modulus of elasticity of the polymer is smaller than $5\times10^5$ dyn/cm$^2$, fine particles of the polymer tends to be fused each other, giving rise to its impaired hair re-setting capability. On the other hand, hardness of the polymer particles increases with the modulus of elasticity exceeding $30\times10^5$ dyn/cm$^2$, providing the hair cosmetic composition with a disagreeable stiff or rough feeling.

According to the present invention, the hair cosmetic composition contains the fine polymer particles in an amount of 0.1–10% by weight (hereinafter designated simply as "%"), preferably 0.4–2%. If the content is below 0.1%, the proper effect of the invention cannot be obtained. On the other hand, the cosmetic composition impairs the feeling to the touch of the hair with the content exceeding 10% of the polymer particles.

The film-forming polymer, component (B), employed in the hair cosmetic composition according to the second invention may be any of those known in the art, which are soluble in a solvent such as water and ethanol. Examples are those listed at the beginning of the chapter entitled "Hair Lacquers or Hair Sprays" of "Cosmetic Science and Technology" [vol. 2, page 352; the second edition (1972)], edited by M. S. Balsam and Edward Sagarin, or at the beginning of the chapter entitled "Hair Spray Resins" of "Hurry's Cosmeticology" [Page 411 (1973)]. Among these, specific examples of desirable compounds are the vinyl monomers (1)–(8) enumerated below:

(1) Polyvinyl pyrrolidone;

(2) Copolymers of vinyl acetate (92.5–87.5%) and crotonic acid (7.5–12.5%) described in U.S. Pat. No. 2,996,471, for example, National Starch Resyn 28-1310.

(3) Terpolymers of vinyl acetate (7–89%), crotonic acid (6–13%), and α-branched aliphatic monocarboxylic acid (5–80%). This aliphatic monocarboxylic acid can be any of those having at least 5 carbon atoms in the carboxyl portion and represented by the formula $R_3C(R_1)(R_2)COOH$ (in which $R_1$ and $R_2$ are alkyl groups, and $R_3$ is selected from a hydrogen atom, or an alkyl, alkalyl or aralkyl or aryl group.). Such terpolymers are described in British Patent No. 1169862 and U.S. Pat. No. 3,810,977, and one of the polymers of this type is commercially available in the trade name of National Starch Resyn 28-2930.

(4) Terpolymers of vinyl acetate, crotonic acid, and a vinyl ester of the formula $R_4-COOCH=CH_2$ (wherein $R_4$ represents a linear or branched hydrocarbon group having 10–22 carbon atoms), or vinyl acetate, crotonic acid, and a alkyl or methacryl ester of the formula $R_5-COOCH_2-C(R_6)=CH_2$ (wherein $R_5$ represents a linear or branched hydrocarbon group having 10–22 carbon atoms and $R_6$ represents a hydrogen atom or a methyl group). Such terpolymers are described in British Patent No. 1153544 and U.S. Pat. No. 3,579,629.

(5) Copolymers of N-vinyl pyrrolidone (20–60%), and such a vinyl acetate as described in U.S. Pat. No. 3,171,784 (40–80%). Such copolymers are commercially sold under the trade names of Luviskol 37E or Luviskol 281.

(6) Copolymers of maleic anhydride (1 mol) and an olefin with 2–4 carbon atoms, typically ethylene (1 mol). This type of copolymer has a molecular weight of 25,000–70,000, and is desirably esterified (esterification degree of as much as 50–70%) by a saturated aliphatic alcohol with 1–4 carbon atoms as described in U.S. Pat. No. 2,957,838.

(7) Such amphoteric acrylic resins as described in U.S. Pat. No. 3,726,288, which are, for example, a terpolymer of acryl amide/acrylate/butylamino-ethylmethacrylate. One of the commercially available products is Amphomer (Trade name).

(8) Copolymers of methylvinyl ether and maleic anhydride with an approximately 1/1 mol ratio. This type of copolymer can be esterified with a saturated aliphatic alcohol with 1-4 carbon atoms, with one example of such an esterified resin being Gantrez ES425 (Trade name).

The content of component (B) in the second invention is 0.1-10%, and particularly preferably is 0.5-2%, of the total weight of the cosmetic. The intended effect of the invention cannot be attained with a content of less than 0.1%. If the content exceeds 10%, on the other hand, the feeling of the hair upon touch of the hair treated by the cosmetic deteriorates.

There is no specific restriction to the forms of the hair cosmetic composition of the present invention, and such forms may be a transparent liquid, lotion, emulsion, spray (aerosol), mousse (foaming aerosol), and the like. Solvents or supporting media of any kind, which are acceptable as a cosmetic, can be used for the hair cosmetic composition of this invention, including, for example, water and lower alcohol (ethanol, isopropanol, and the like). These can be used either individually or mixed with one or more solvents. When the hair cosmetic composition takes the form of an aerosol, fluorocarbon, liquefied petroleum gas, dimethyl ether, or the like are used as a propellant. These can also be used individually or mixed with one or more other types, and may desirably be used in an amount of 1-20% of the total weight of the hair cosmetic composition, i.e., the amount which brings the internal pressure of the container in which the aerosol-type hair cosmetic composition is contained to 2.0-6.0 kg/cm$^2$G.

Besides the above-mentioned ingredients, various kinds of cosmetic oils can be formulated into the hair cosmetic composition of this invention, inasmuch as the effect of the invention is not impaired, e.g. 0.1-10%. Oil or fat ingredients which are suitably employed are, for example, triglycerides such as castor oil, coconut oil, mink oil, avocado oil, olive oil, and the like; waxes such as bees wax, sperm oil, lanolin, carnauba wax, and the like; alcohols such as cetyl alcohol, oleyl alcohol, hexadecyl alcohol, lauryl alcohol, stearyl alcohol, isostearyl alcohol, 2-octyldodecanol, polypropylene glycol, and the like; esters such as isopropyl myristate, hexyl laurate, cetyl lactate, propylene glycol monostearate, oleyl oleate, hexadecyl 2-ethylhexanoate, octyldodecyl myristate, and the like; silicone derivatives such as dimethylpolysiloxane, methylphenylpolysiloxane, polyether-modified silicone oil, epoxy-modified silicone oil, amino-modified silicone oil, alkyl-modified silicone oil and the like. In addition, emulsifiers can be added in order to emulsify these oils or fats. The emulsifiers can be any surface active agents, including anionic, amphoteric, cationic, and nonionic types.

Furthermore, perfumes or coloring agents can be added for the purpose of promoting the commercial value of the hair cosmetic composition. Also, in order to prevent the hair cosmetic composition from deteriorating after a lapse in time, antiseptics or antioxidants, or moisture adjusting agents such as glycerin, propylene glycol, and the like, can be formulated.

The hair cosmetic composition of the present invention containing fine particles of crosslinked polymer produces a satisfactory feeling to the users upon use, and provides excellent hair conditioning as well as reconditioning effects. It can be widely applied to hair cosmetic compositions for men and women, young as well as for the elderly. Furthermore, hair cosmetic composition can be provided with flexible hair conditioning capability for accommodating the preferences of a wide variety of users by changing the amount of the fine particles of the crosslinked polymer or by additionally formulating component (B) of the second invention.

Other features of the invention will become apparent in the course of the following description of the exemplary embodiments which are given for illustration of the invention and are not intended to be limiting thereof.

EXAMPLES

In the synthetic examples below, the adhesion and modulus of elasticity of polymers were measured according to the following methods.

Measurement of Adhesion 0.5 gm of a 20% aqueous suspension of the fine polymer particles was coated on a glass plate of 76×26 mm, and dried completely. Also, 2 gm of the same aqueous suspension of the fine polymer particles was coated on the one side of a polyethylene film of 100×18 mm, and completely dried. The the glass plate and polyethylene film were then put together with the coated surfaces face to face, and pressed 5 times with a hand roller with a 5 kg.f load. Then, the test specimen thus prepared was subjected to a 90° peel strength test at 20° C. and 65% relative humidity and at a peeling-off rate of 20 mm/min using a TCM-20S tension tester (manufactured by Shinkoh Co., Ltd.) to obtain a stress chart. The 0-15% and 85-100% sections of the original graph were discarded. The actual values of the remaining curve at 0%, 25%, 50%, 75%, and 100% were totalled and averaged. This value was taken as the value for adhesion.

Measurement of Modulus of Elasticity

A thermal stress strain tester TMA/SS10 (manufactured by Seiko I & E Co., Ltd.) was used for the measurement.

A sphere with a 5 mm diameter of the fine polymer particles was longitudinally pressed in a probe with a base area of 0.01 $\pi$mm$^2$ at a initial stress of 2 gm, with subsequent vibrations at a prescribed wave length (0.02 Hz, 2±2 gm). The modulus of elasticity was determined from the rate of strain changes due to the press.

Synthetic Example 1

The following compositions, (A) and (B), were provided.

| | |
|---|---|
| Composition (A): | |
| Polyvinyl alcohol | 2.3 gm |
| (Gosenol GH-17, manufactured by Nihon Gosei Kagaku Kogyo Co., Ltd.; saponification value: 86.5-89 mol %, viscosity: 27-33 cps) | |
| Water | 230 gm |
| Composition (B): | |
| n-lauryl acrylate | 100 gm |
| divinyl benzene | 1.0 gm |
| peroxy lauroyl | 2 gm |

The homogeneous solution of the above composition (B) was added to composition (A), and mixed by homogenizer until component (B) solution was dispersed in the component (A) solution. The dispersed solution was transferred to a 1,000 ml separable flask equipped particle size of each polymer were measured. The results are shown in Table 2.

TABLE 2

| Synthetic Examples | Monofunctional oil-soluble monomer | | Polyfunctional oil-soluble monomer | | Adhesion (g · f/cm) | Modulus of Elasticity (dyn/cm$^2$) | Weight Average Particle Diameter (μm) |
|---|---|---|---|---|---|---|---|
| 4 | 2-ethylhexyl acrylate | 100 gm | divinyl benzene | 0.2 gm | 70 | $10 \times 10^5$ | 3.0 |
| 5 | 2-ethylhexyl acrylate | 100 gm | divinyl benzene | 2.0 gm | 50 | $10 \times 10^5$ | 2.5 |
| 6 | n-butyl acrylate | 100 gm | divinyl benzene | 2.0 gm | 50 | $15 \times 10^5$ | 3.0 |
| 7 | n-lauryl methacrylate | 100 gm | ethylene glycol diacrylate | 0.5 gm | 70 | $15 \times 10^5$ | 4.0 |
| 8 | 2-ethylvinyl ether | 100 gm | ethylene glycol propane acrylate | 0.2 gm | 54 | $10 \times 10^5$ | 3.0 |
| 9 | 2-ethylhexyl acrylate | 100 gm | ethylene glycol dimethacrylae | 7.0 gm | 97 | $15 \times 10^5$ | 5.0 |
| 10 | 2-ethylhexyl acrylate | 100 gm | polyethylene glycol #200 dimethacrylate | 7.0 gm | 10 | $25 \times 10^5$ | 5.0 | with a stirrer, condenser, thermometer, and nitrogen gas introducing tube, and heated at 80° C. for 8 hours while gently stirring. The contents of the flask were then filtered, washed with water, and again filtered, followed by drying in vacuo. The fine particles of crosslinked polymer thus obtained were insoluble in water and ethanol, and had a weight average particle size of 20 μm.

The adhesion and modulus of elasticity determined according to the methods described above were 20 g.f/cm and $8 \times 10^5$ dyn/cm$^2$, respectively. These polymer particles exhibited excellent hair setting and re-setting capability when applied to the hair, and provided a satisfactory feeling to the touch without stickiness, roughness as well as any disagreeable feeling.

Synthetic Examples 2 and 3

The fine particles of crosslinked polymers listed in Table 1 were prepared in the same manner as described in Synthetic Example 1, except that divinyl benzene (polyfunctional oil-soluble monomer) were used in the amounts as shown in Table 1.

TABLE 1

| Synthetic Examples | Monofunctional oil-soluble monomer | | Polyfunctional oil-soluble monomer | | Adhesion (g · f/cm) | Modulus of Elasticity (dyn/cm$^2$) | Weight Average Particle Diameter (μm) |
|---|---|---|---|---|---|---|---|
| 2 | n-lauryl acrylate | 100 gm | divinyl benzene | 1.5 gm | 60 | $15 \times 10^5$ | 2.5 |
| 3 | 2-ethylhexyl acrylate | 100 gm | divinyl benzene | 0.05 gm | 100 | $2 \times 10^5$ | 3.5 |

The adhesion and modulus of elasticity were determined according to the methods described above on each of the product. Also, the weight average particle size of each polymer were measured. The results are shown in Table 1.

The products of Synthetic Examples 2 and 3 had both suitable adhesion and modulus of elasticity, and when applied to the hair, provided a satisfactory feeling, and exhibited excellent hair setting and re-setting capability.

Synthetic Examples 4-10

The fine particles of crosslinked polymers listed in Table 2 were prepared using monofunctional oil-soluble monomer and polyfunctional oil-soluble monomer listed in Table 2. The adhesion and modulus of elasticity were determined according the methods described above on each of the product. Also, the weight average The fine particles of crosslinked polymers obtained were insoluble in water and ethanol.

All of the products produced in Synthetic Examples 4-10 exhibited an excellent hair setting capability and imparted a satisfactory feeling.

EXAMPLE 1

A hair cream with the following formulation was prepared according to a conventional method.

| | |
|---|---|
| Fine particles of polymer prepared in Synthetic Example 1 | 1.0% |
| Polyoxyethylenestearyl ether | 1.5% |
| Bees wax | 1.0% |
| Perfume | Suitable amount |
| Antiseptic | Suitable amount |
| Water | Balance |
| Total | 100 |

EXAMPLE 2

A hair liquid with the following formulation was prepared according to a conventional method.

| | |
|---|---|
| Fine particles of polymer prepared in Synthetic Example 4 | 0.5% |
| Propylene glycol | 2.0% |
| Ethanol | 45.0% |
| Perfume | Suitable amount |
| Coloring agent | Suitable amount |
| Water | Balance |
| Total | 100 |

EXAMPLE 3

A hair conditioner with the following formulation was prepared according to a conventional method.

| | |
|---|---|
| Fine particles of polymer prepared in Synthetic Example 5 | 1.0% |

| | |
|---|---|
| Cetyltrimetylammonium chloride | 0.75% |
| Setostearyl alcohol | 1.0% |
| Glyceryl monostearate | 0.5% |
| Perfume | Suitable amount |
| Water | Balance |
| Total | 100 |

EXAMPLE 4

A foaming hair conditioner (mousse) with the following formulation was prepared according to a conventional method.

| | |
|---|---|
| Hair conditioner prepared Example 3 | 90.0% |
| Propellant | 10.0% |
| Total | 100 |

(A mixture of 60% Freon 12 and 40% Freon 114 was used as the propellant)

EXAMPLE 5

A hair liquid with the following formulation was prepared according to a conventional method.

| | |
|---|---|
| Fine particles of polymer prepared in Synthetic Example 6 | 2.0% |
| PVP K30 (polyvinyl pyrrolidone, manufactured by GAF Co.) | 1.5% |
| Propylene glycol | 3.0% |
| Ethanol | 40.0% |
| Perfume | Suitable amount |
| Water | Balance |
| Total | 100 |

EXAMPLE 6

A foaming hair conditioner (mouse) was prepared by filling a pressure container with a base liquid (L) with the following formulation and the propellant (G), at a ratio of L/G=90/10.

| | |
|---|---|
| Fine particles of polymer prepared in Synthetic Example 7 | 1.5% |
| Gantretz ES 425 | 0.5% |
| Cetyltrimetylammonium chloride | 0.1% |
| Ethanol | 10.0% |
| Perfume | Suitable amount |
| Water | Balance |
| Total | 100 |

(A mixture of 60% Freon 12 and 40% Freon 114 was used as the propellant.)

EXAMPLE 7

A hair liquid with the following formulation was prepared according to a conventional method.

| | |
|---|---|
| Fine particles of polymer prepared in Synthetic Example 8 | 0.4% |
| Resyn 28-1310 | 2.0% |
| Glycerine monostearate | 1.2% |
| Cetyltrimetylammonium chloride | 0.5% |
| Ethanol | 45.0% |
| Perfume | Suitable amount |
| Water | Balance |
| Total | 100 |

The hair cosmetic composition prepared in the above Examples 1-7, when applied to the hair in a usually employed amount, exhibited excellent hair conditioning and re-conditioning effects, without giving any unacceptable feeling such as roughness, stickiness, or stiffness.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

1. The hair cosmetic composition comprising:
   (A) fine particles of a crosslinked polymer which is derived from a monofunctional oil-soluble monomer having one ethylenically unsaturated bond, of which polymer having a glass transition point of not higher than 300° K., are insoluble in water and ethanol, and do not form a film at normal temperature, wherein said fine particles of a crosslinked polymer having an adhesion of 8-100 g.f/cm and modulus of elasticity of $5 \times 10^5 - 30 \times 10^5$ dyn/cm$^2$ and
   (B) a film-forming polymer.
2. The hair cosmetic composition as claimed in claim 1, wherein the content of component (A) is 0.1-10% by weight and the content of component (B) is 0.1-10% by weight.

* * * * *